US00PP15786P2

(12) United States Plant Patent
Hanes

(10) Patent No.: US PP15,786 P2
(45) Date of Patent: Jun. 7, 2005

(54) *PETUNIA* PLANT NAMED 'WHIP ROSEIN'

(50) Latin Name: *Petunia×hybrida*
Varietal Denomination: Whip Rosein

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 55 days.

(21) Appl. No.: 10/818,347

(22) Filed: Apr. 5, 2004

(51) Int. Cl.[7] ..... A01H 5/00
(52) U.S. Cl. ..... Plt./356
(58) Field of Search ..... Plt./356

(56) References Cited

U.S. PATENT DOCUMENTS

PP12,139 P2 * 10/2001 Rother ..... Plt./356
PP14,856 P2 * 6/2004 Sakazaki ..... Plt./356
PP15,002 P2 * 7/2004 Strope ..... Plt./356

OTHER PUBLICATIONS

UPOV ROM GTITM Computer Database, GTI Jouve Retrieval Software 2004/04 Citations for 'Whip Rosein'.* http:www.theflowerfields.com/ffa/grower.aspx?tabid=298&cat=veg_Yoder&id=3502.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Petunia* plant named 'Whip Rosein', characterized by its low trailing, outwardly spreading and mounded plant habit; freely branching habit; freely flowering habit; single flowers that are red purple in color with darker red purple-colored venation; and good garden performance.

1 Drawing Sheet

Botanical classification/cultivar designation: *Petunia×hybrida* cultivar Whip Rosein.

BACKGROUND OF THE INVENTION

The present Invention relates to a new and distinct cultivar of *Petunia* plant, botanically known as *Petunia×hybrida,* and hereinafter referred to by the cultivar name Whip Rosein.

The new *Petunia* is a product of a planned breeding program conducted by the Inventor in Gilroy, Calif. The objective of the breeding program is to create new freely flowering *Petunias* with trailing and spreading plant habit and attractive leaf and flower coloration.

The new *Petunia* originated from a cross-pollination made by the Inventor in September, 2000 of a proprietary selection of *Petunia×hybrida* identified as code number 00-382-4, not patented, as the female, or seed parent, with a proprietary selection of *Petunia×hybrida* identified as code number 00-381-2, not patented, as the male, or pollen parent. The new *Petunia* was selected as a single plant from the resulting progeny of the cross-pollination in a controlled environment in Gilroy, Calif. in March, 2001.

Asexual reproduction of the new cultivar by terminal vegetative cuttings since March, 2001, in Gilroy, Calif. has shown that the unique features of this new *Petunia* are stable and reproduced true to type in successive generations.

SUMMARY OF THE INVENTION

Plants of the cultivar Whip Rosein have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Whip Rosein'. These characteristics in combination distinguish 'Whip Rosein' as a new and distinct cultivar:

1. Low trailing, outwardly spreading and mounded plant habit.
2. Freely branching habit.
3. Freely flowering habit.
4. Single flowers that are red purple in color with darker red purple-colored venation.
5. Good garden performance.

In side-by-side comparisons conducted in Gilroy, Calif., plants of the new *Petunia* differed from plants of the female parent selection in the following characteristics:

1. Plants of the new *Petunia* were more vigorous than plants of the female parent selection.
2. Plants of the new *Petunia* had smaller flowers than plants of the female parent selection.
3. Plants of the new *Petunia* and the female parent selection differed in flower color as plants of the female parent selection had purple-colored flowers.

In side-by-side comparisons conducted in Gilroy, Calif., plants of the new *Petunia* differed from plants of the male parent selection in the following characteristics:

1. Plants of the new *Petunia* had smaller flowers than plants of the male parent selection.
2. Plants of the new *Petunia* and the male parent selection differed in flower color as plants of the male parent selection had scarlet-colored flowers.

Plants of the new *Petunia* differ from plants of the *Petunia* cultivar Whip Pur, disclosed in U.S. Plant patent application Ser. No. 10/818,375, primarily in flower color.

Plants of the new *Petunia* can be compared to plants of the cultivar Surfinia Pink Mini 2000, not patented. In side-by-side comparisons conducted in Gilroy, Calif., plants of the new *Petunia* differed from plants of the cultivar Surfinia Pink Mini 2000 in the following characteristics:

1. Plants of the new *Petunia* were smaller than plants of the cultivar Surfinia Pink Mini 2000.
2. Plants of the new *Petunia* and the cultivar Surfinia Pink Mini 2000 differed in flower color as plants of the cultivar Surfinia Pink Mini 2000 had lavender-colored flowers.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Petunia*.

The photograph at the top of the sheet comprises a side perspective view of a typical plant of 'Whip Rosein' grown in a container.

The photograph at the bottom of the sheet is a close-up view of typical flowers and leaves of 'Whip Rosein'.

DETAILED BOTANICAL DESCRIPTION

Plants of the cultivar Whip Rosein have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the summer with day temperatures ranging from 24 to 29° C., night temperatures ranging from 13 to 18° C. and light levels about 2,000 foot-candles. Plants used for the photographs and description were about 12 weeks from planting rooted cuttings. In the following description, color references are made to The Royal Horticultural Society Colour Chart, 1995 Edition, except where general terms of ordinary dictionary significance are used.

Botanical classification: *Petunia×hybrida* cultivar Whip Rosein.

Parentage:

*Female parent.*—Proprietary selection of *Petunia×hybrida* identified as code number 00-382-4, not patented.

*Male parent.*—Proprietary selection of *Petunia×hybrida* identified as code number 00-381-2, not patented.

Propagation:

*Type cutting.*—Terminal vegetative cuttings.

*Time to initiate roots, summer and winter.*—About 10 to 12 days at 23° C.

*Time to develop roots, summer and winter.*—About 18 to23 days at 23° C.

*Root description.*—Fine, fibrous; white in color.

*Rooting habit.*—Freely branching.

Plant description:

*Form.*—Annual flowering plant; indeterminate; initially upright, then low trailing and outwardly spreading; uniformly mounded plant form. Freely branching habit; about eight basal branches each with about four to six lateral branches. Pinching enhances development of lateral branches.

*Usage.*—Appropriate for hanging baskets, window boxes, patio containers and landscape applications.

*Plant height.*—About 20 cm.

*Plant diameter* (*area of spread*).—About 55 cm.

*Vigor.*—Vigorous; rapid growth rate.

*Lateral branches.*—Length: About 32 cm. Diameter: About 4.5 mm. Internode length: About 3.5 cm. Texture: Pubescent. Color: 144C.

*Foliage description.*—Arrangement: Alternate before flowering; opposite after flowers develop; simple. Length: About 5.3 cm. Width: About 3.2 cm. Shape: Elliptic. Apex: Broadly acute. Base: Attenuate. Margin: Entire. Texture, upper and lower surfaces: Sparsely pubescent; glandular. Venation pattern: Pinnate, arcuate. Color: Developing and fully expanded leaves, upper surface: 147A. Developing and fully expanded leaves, lower surface: 147B. Venation, upper surface: 146C. Venation, lower surface: 147C. Petiole length: About 1 cm. Petiole diameter: About 2.5 mm. Petiole color, upper and lower surfaces: 146C. Petiole texture: Sparsely pubescent.

Flower description:

*Flower type and habit.*—Single salverform flowers; flowers face mostly upward or outward; axillary. Freely flowering habit, about two to three open flowers and about three flower buds per lateral branch at one time.

*Natural flowering season.*—Long day responsive; long flowering period, spring until frost in the autumn; flowering continuous during this period. Plants start flowering about eight weeks after planting rooted cuttings. Flowers persistent.

*Flower longevity on the plant.*—About seven to ten days.

*Fragrance.*—Faint, sweet.

*Flower size.*—Diameter: About 4.5 cm. Tube length: About 2.3 cm. Throat diameter, distal end: About 8 mm. Tube diameter, proximal end: About 3 mm.

*Flower buds.*—Length: About 2.8 cm. Diameter: About 5 mm. Shape: Elongated oblong with ruffled apices. Color: More gray than 78B.

*Petals.*—Quantity/arrangement: About five petals fused in a single whorl, funnelform. Length from throat: About 2 cm. Width: About 2 cm. Shape: Roughly fan-shaped. Apex: Acute. Margin: Entire; undulate. Texture, upper and lower surfaces: Smooth, velvety. Color: When opening, upper surface: 67B; venation, 57A. When opening, lower surface: 70C; venation, 146C. Fully opened, upper surface: 67C; venation, 66A. Fully opened, lower surface: 73C; venation, 146C. Flower throat (inside): 75C. Flower tube (outside): 75B. Venation, throat: 199C. Venation, tube: 146D.

*Sepals.*—Arrangement/appearance: Single whorl of five sepals fused at base, star-shaped. Length: About 1.2 cm. Width: About 3 mm. Shape: Ligulate. Apex: Rounded. Margin: Entire. Texture, upper and lower surfaces: Pubescent. Color, upper surface: 146A. Color, lower surface: 146B.

*Peduncles.*—Length: About 4.1 cm. Width: About 1.25 mm. Angle: About 45 to 60° from the stem. Strength: Strong. Texture: Pubescent. Color: 144A.

*Reproductive organs.*—Stamens: Quantity per flower: About five. Anther shape: Ovoid. Anther size: About 1.5 mm by 2 mm. Anther color: 155A. Pollen amount: Scarce. Pollen color: 155A. Pistils: Quantity per flower: One. Pistil length: About 2 cm. Style length: About 1.7 cm. Style color: 144D. Stigma shape: Anvil-shaped. Stigma color: 146A. Ovary color: 145A.

*Seed/fruit.*—Seed and/or fruit production has not been observed.

Disease/pest resistance: Plants of the new *Petunia* have not been noted to be resistant to pathogens or pests common to *Petunia.*

Garden performance: Plants of the new *Petunia* have been observed to have good garden performance. Plants of the new *Petunia* have been noted to tolerate rain, wind and temperatures from 0 to 40° C.

It is claimed:

1. A new and distinct cultivar of *Petunia* plant named 'Whip Rosein', as illustrated and described.

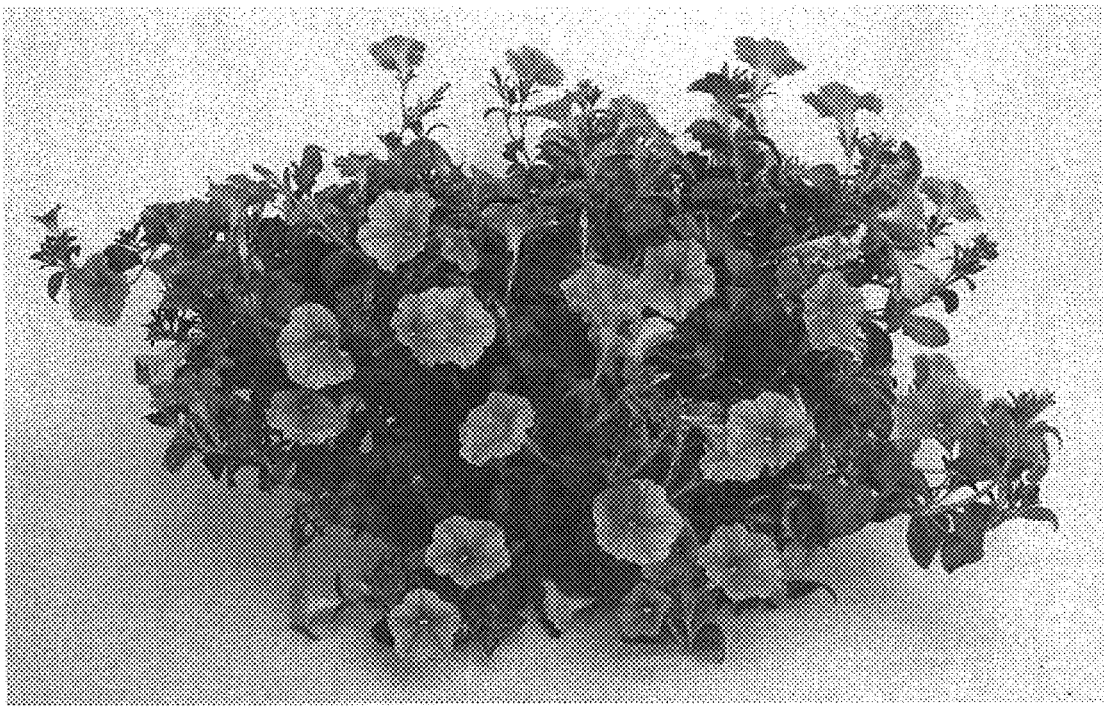
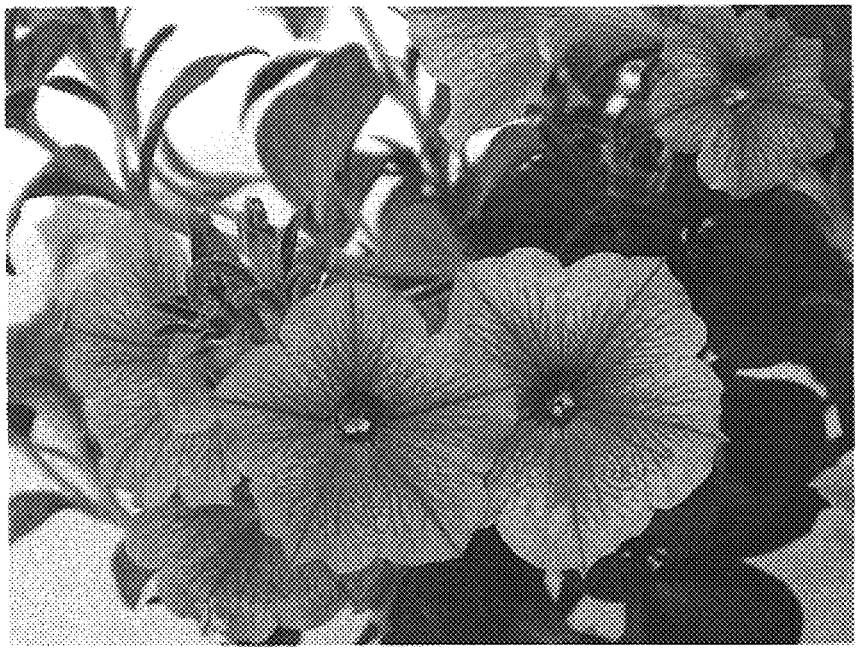

* * * * *